(12) United States Patent
Evans

(10) Patent No.: US 7,217,358 B2
(45) Date of Patent: May 15, 2007

(54) ULTRAVIOLET RADIATION TREATMENT OF UNWANTED MICROORGANISMS

(76) Inventor: Lionel Evans, 227 Jericho Road, Pukekohe (NZ)

( * ) Notice: Subject to any disclaimer, the term of this patent is extended or adjusted under 35 U.S.C. 154(b) by 0 days.

(21) Appl. No.: 10/512,941

(22) PCT Filed: Apr. 28, 2003

(86) PCT No.: PCT/NZ03/00073

§ 371 (c)(1),
(2), (4) Date: Jun. 10, 2005

(87) PCT Pub. No.: WO03/092392

PCT Pub. Date: Nov. 13, 2003

(65) Prior Publication Data

US 2005/0230320 A1     Oct. 20, 2005

(30) Foreign Application Priority Data

Apr. 30, 2002    (NZ) .................................. 518658

(51) Int. Cl.
*C02F 1/32* (2006.01)

(52) U.S. Cl. ................... 210/195.1; 210/196; 210/259; 210/748; 250/438

(58) Field of Classification Search ................ 210/192, 210/195.1, 196, 259, 262, 748; 99/483, 534, 99/536; 426/248; 250/343, 435, 438; 422/23, 422/186.3
See application file for complete search history.

(56) References Cited

U.S. PATENT DOCUMENTS

| | | | |
|---|---|---|---|
| 4,141,830 A | 2/1979 | Last | 210/63 |
| 4,273,660 A | 6/1981 | Beitzel | 210/760 |
| 5,405,631 A * | 4/1995 | Rosenthal | 426/235 |
| 5,925,395 A | 7/1999 | Chen | 426/321 |
| 5,939,117 A | 8/1999 | Chen et al. | 426/267 |
| 5,994,704 A | 11/1999 | Nakasuji | 250/396 |
| 5,994,705 A | 11/1999 | Cooke et al. | 250/438 |
| 6,015,229 A | 1/2000 | Cormack et al. | 366/336 |
| 6,080,313 A * | 6/2000 | Kelada | 210/631 |
| 6,099,799 A | 8/2000 | Anderson | 422/24 |
| 6,193,894 B1 | 2/2001 | Hollander | 210/748 |

(Continued)

FOREIGN PATENT DOCUMENTS

SU    1593216 A1 *   10/1995

(Continued)

OTHER PUBLICATIONS

Patent Abstracts of Japan, vol. 1996, No. 7, Jul. 31, 1996, & JP08066677A (Honda Hajime), Mar. 12, 1996.

(Continued)

*Primary Examiner*—Matthew O. Savage
(74) *Attorney, Agent, or Firm*—Jacobson Holman PLLC

(57) ABSTRACT

A method and apparatus are described for killing or inhibiting growth of undesired microorganisms using ultraviolet radiation. A vortex turbulated flow of water is established within a vertical tube through which is transmitted ultraviolet radiation. In a preferred embodiment the dwell time of water within the tube may be varied to achieve optimum exposure. The method can be used to treat water alone or to treat objects suspended in water. In a particularly preferred embodiment freshly cut pieces of fruit may be treated.

14 Claims, 5 Drawing Sheets

U.S. PATENT DOCUMENTS

| | | |
|---|---|---|
| 6,501,079 B1 * | 12/2002 | Furuya ...................... 250/437 |
| 2001/0047964 A1 | 12/2001 | Matherly et al. ........... 210/748 |

FOREIGN PATENT DOCUMENTS

| | | |
|---|---|---|
| SU | 2139115 A1 * | 10/1999 |
| WO | WO94/02680 | 2/1994 |
| WO | WO95/28846 | 11/1995 |
| WO | WO 97/46271 * | 12/1997 |
| WO | WO02/072480 | 9/2002 |

OTHER PUBLICATIONS

Patent Abstracts of Japan, vol. 1995, No. 11, Dec. 26, 1995, & JP07204670A (Masayoshi Kodesen; others), Aug. 8, 1995.

* cited by examiner

ULTRAVIOLET RADIATION TREATMENT OF UNWANTED MICROORGANISMS

This is a nationalization of PCT/NZ03/00073 filed Apr. 28, 2003 and published in English.

TECHNICAL FIELD

This invention relates to a method and apparatus for killing or inhibiting growth of undesired microorganisms with ultraviolet radiation. In one embodiment, the apparatus and method of the invention are used for treating undesired microorganisms on whole and cut fresh fruit and vegetables with ultraviolet radiation to enhance their shelf life. In another embodiment the method and apparatus are used to kill undesired microorganisms in waste water.

BACKGROUND ART

Ultraviolet radiation systems are known for the treatment of water. In one type of system an ultraviolet bulb or tube is mounted in a housing which is transparent to ultraviolet radiation. This is surrounded by a vertically oriented annular chamber containing water to be treated. In some embodiments the ultraviolet radiation is used to generate ozone to sterilise the water. In other embodiments the ultraviolet radiation provides the sterilisation directly. Representative patents of such technology are U.S. Pat. No. 4,141,830; US 4,273,660; US 6,099,799 and US 6,193,894.

It is also known from U.S. Pat. No. 6,015,229 to disinfect fluid by passing fluid flow through a uniform array of ultraviolet lamps having cross-sections perpendicular to the direction of fluid flow. Flow defecting delta wings are positioned to create pairs of vortices that either rotate in the same direction or in directions opposed to one another to assist in mixing the fluids while exposing them to ultraviolet radiation.

In U.S. Pat. No. 5,994,704 there is also described a flowthrough photochemical reactor using ultraviolet radiation. Deflectors are imposed in the flow path to create a turbulent flow to increase the uniformity of the fluid's exposure to photons radiating from a source within a tube. The flow path is substantially annular to that central source.

It would be desirable to provide a system to kill or inhibit growth of microorganisms suspended or dissolved in water by ultraviolet radiation. In order to ensure as complete a kill as is required the time of exposure of the microorganisms should be able to be controlled in a simple manner.

It is an object of this invention to go some way towards achieving this desideratum or at least to offer the public a useful choice.

SUMMARY OF THE INVENTION

Accordingly the invention may be said broadly to consist in a method for killing or inhibiting the growth of microorganisms in water which comprises:
  establishing a vortex turbulated flow of water containing said microorganisms through a vertically oriented ultraviolet light transparent tube which is open at both ends,
  generating a flow of ultraviolet radiation into said tube and through said vortex flow, whereby said microorganisms are exposed to said ultraviolet radiation while passing down said tube, and
  recovering said water after it has exited said tube.

Preferably said vortex is augmented by projecting a jet of water containing said microorganism substantially tangentially into said tube at or adjacent the top thereof.

Preferably the rate of flow of said jet is controlled so as to control the dwell time of said microorganisms in said tube.

In one alternative the strength of said ultraviolet radiation is varied while said microorganisms are exposed in said tube.

Preferably said microorganisms are on objects in said vortex turbulated flow.

Preferably said objects are recovered after they have exited said tube.

Preferably said objects are comestibles.

Preferably said comestibles are vegetables or fruit.

More preferably said comestibles are freshly cut fruit.

Preferably said comestibles have been permeated with a preserving agent before being placed in said vortex flow.

Preferably said comestibles are dried after exiting said tube.

Preferably said ultraviolet radiation has a wavelength of 200 to 280 nanometers.

Most preferably said ultraviolet radiation has a wavelength of 253.7 nanometers.

Preferably the temperature of said vortex flow when said microorganisms are exposed to said ultraviolet radiation is at about 42° C.

The invention may also be said broadly to consist in an apparatus for killing or inhibiting the growth of microorganisms in water or which comprises:
  a vertically oriented tube which is transparent to ultraviolet radiation, said tube having a top end and a bottom end,
  means to supply water into said top end in a manner which establishes a vortex flow in said tube,
  ultraviolet radiating means surrounding said tube adapted to radiate ultraviolet radiation through said tube and water containing said microorganisms therein, and
  draining means from said bottom end of said tube.

Preferably said tube is constructed of a fluoropolymer.

In one alternative said means for supplying said water into said tube comprises a funnel having a spiral flow path therethrough.

In another alternative there is provided a tangential water jet to impart a controllable vortex turbulation within said tube in combination with said funnel.

In a still further embodiment there is provided a tangential water jet as the sole means for supplying said water containing said microorganisms.

Preferably said ultraviolet radiating means is a low pressure mercury vapour quartz tube.

Preferably said low pressure mercury vapour quartz tube radiates ultraviolet radiation at a wavelength of 253.7 nanometers.

Preferably there is a casing surrounding said ultraviolet radiating means, the inner face of said casing having reflecting means for reflecting ultraviolet radiation.

Preferably there is a temperature control system associated with said tube and said ultraviolet radiating means for controlling the temperature at which said ultraviolet radiation is radiated.

Preferably there is a temperature control means for controlling the temperature of said water flowing through said tube.

Preferably said draining means is a pipe.

Preferably there is provided an infeed tank upstream of said means to supply water into said tube.

Preferably there is a means for continuously feeding comestibles into said infeed tank.

Preferably there is a holding tank downstream of said draining means into which said draining means may discharge water and comestibles that have passed through said tube.

Preferably there are means to convey comestibles out of said holding tank.

Preferably there are means for recycling water from said holding tank to said infeed tank.

Preferably said means to recycle said water comprises a main tank, a pipe discharging water from said holding tank to said main tank, conduit means from said main tank to said infeed tank, a pump and a filtering system in said conduit means, the distal end of said conduit means returning water into said infeed tank.

The invention may also be said broadly to consist in an apparatus substantially as herein described with reference to FIGS. 1 to 6.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The invention may be more fully understood by having reference to the accompanying drawings in which.

DETAILED DESCRIPTION OF THE INVENTION

Construction of the Apparatus

Figure 1:
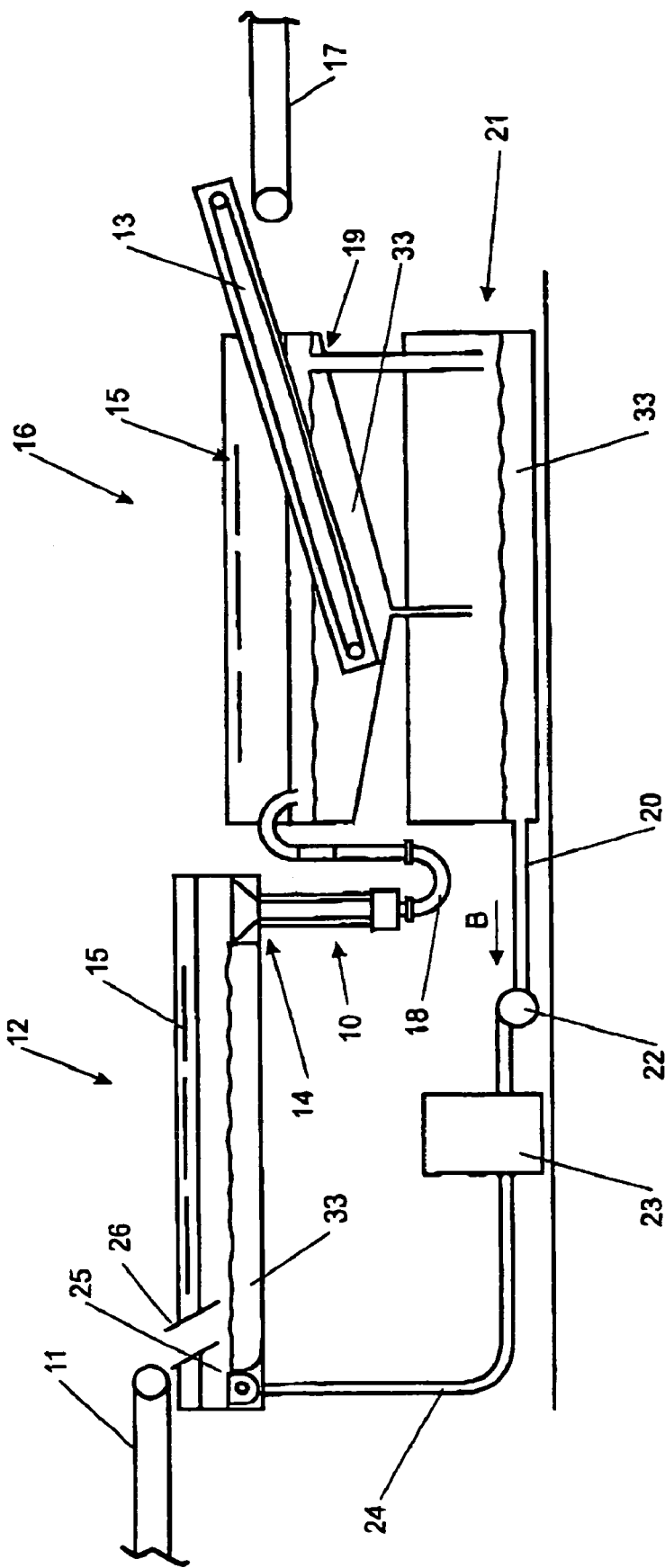
FIG. 1 is a side elevational schematic view of all the components associated with the treatment apparatus according to one embodiment of the invention.

The apparatus consists of an infeed tank 12, a holding tank 16 and a main tank 21. The ultraviolet radiation treatment part of the apparatus is housed in chamber 10, the construction of which will be described in more detail with reference to FIG. 2 below. Infeed tank 12 is provided with a cover 15 to keep out contamination. An infeed conveyor 11 is aligned with chute 26 to supply product (such as comestibles) into tank 12. Within tank 12 is treatment fluid 33. The treatment fluid may be water or water containing preservatives known to those skilled in the art. When the product is sliced fresh fruit a 1–7% (W/W) solution of calcium hydroxide may be used.

At the upstream end of infeed tank 12 there is a weir 25 over which fluid from pipe 24 is supplied into infeed tank 12.

At the downstream end of tank 12 is a funnel 14, the construction of which will be discussed in relation to FIG. 3.

The lower end of treatment chamber 10 is connected to an outlet pipe 18 which has two 180° bends and ends with its mouth open to discharge liquid into holding tank 16. Holding tank 16 is also provided with a cover 15 to keep out contamination. The bottom of holding tank 16 is substantially v-shaped in cross-section to accommodate an outfeed conveyor 13. Outfeed conveyor 13 is arranged above a further conveyor 17 to convey treated comestibles for further processing.

A pipe 19 is arranged as illustrated to discharge treatment fluid into main tank 21. Main tank 21 has a return pipe 20 leading to a pump 22. This in turn leads to a filtration system 23. A further return pipe 24 connects to weir 25 to complete the circuit.

A peristaltic pump (not shown) injects super-saturated calcium makeup solution into main tank 21 as required.

The construction of the ultraviolet radiation chamber 10 is described with reference to FIG. 2. The chamber will be described starting with the central passage and moving radially outward. A tube 34 made from an advanced fluoropolymer which is transparent to ultraviolet radiation (AFP-840™) defines a passage 36 extending from funnel 14 to outlet pipe 18. The tube 34 is held in position at either end by compression rings 32 and in between by compression bands 35. The rings 32 are preferably stainless steel hose clips. Their purpose is to stop leakage.

In the annular chamber 39 surrounding tube 34 there are positioned a series of ultraviolet radiating tubes 30. In the preferred embodiment these tubes are of a low pressure mercury vapour quartz type. The optimum ultraviolet radiation wavelength to achieve maximum germicidal activity is 253.7 nanometers. This is considered to be 100% efficient when the lamps' surface temperature is 42.2° C.

The tubes 30 are held at either end in tube holders 29. These are powered by a wiring loom 31.

To the outside of the annular chamber 39 surrounding tube 36 is a cylindrical reflector shield 28. Preferably the inner reflective surface 28 is brushed aluminium which is highly reflective to ultraviolet radiation.

The ultraviolet radiating chamber construction is completed by a cylindrical outside casing 27 which may be made of stainless steel. At the bottom of the chamber 10 is a base plate 38.

From the bottom end of tube 34 there is a funnel-shaped portion 37 which joins the bottom end of passage 36 to the end of outlet pipe 18. In the embodiment illustrated in FIG. 2 there is a sleeve fitting 43 over an open end of pipe 18 leading to an extension of this pipe as shown in FIG. 1.

Figure 3:
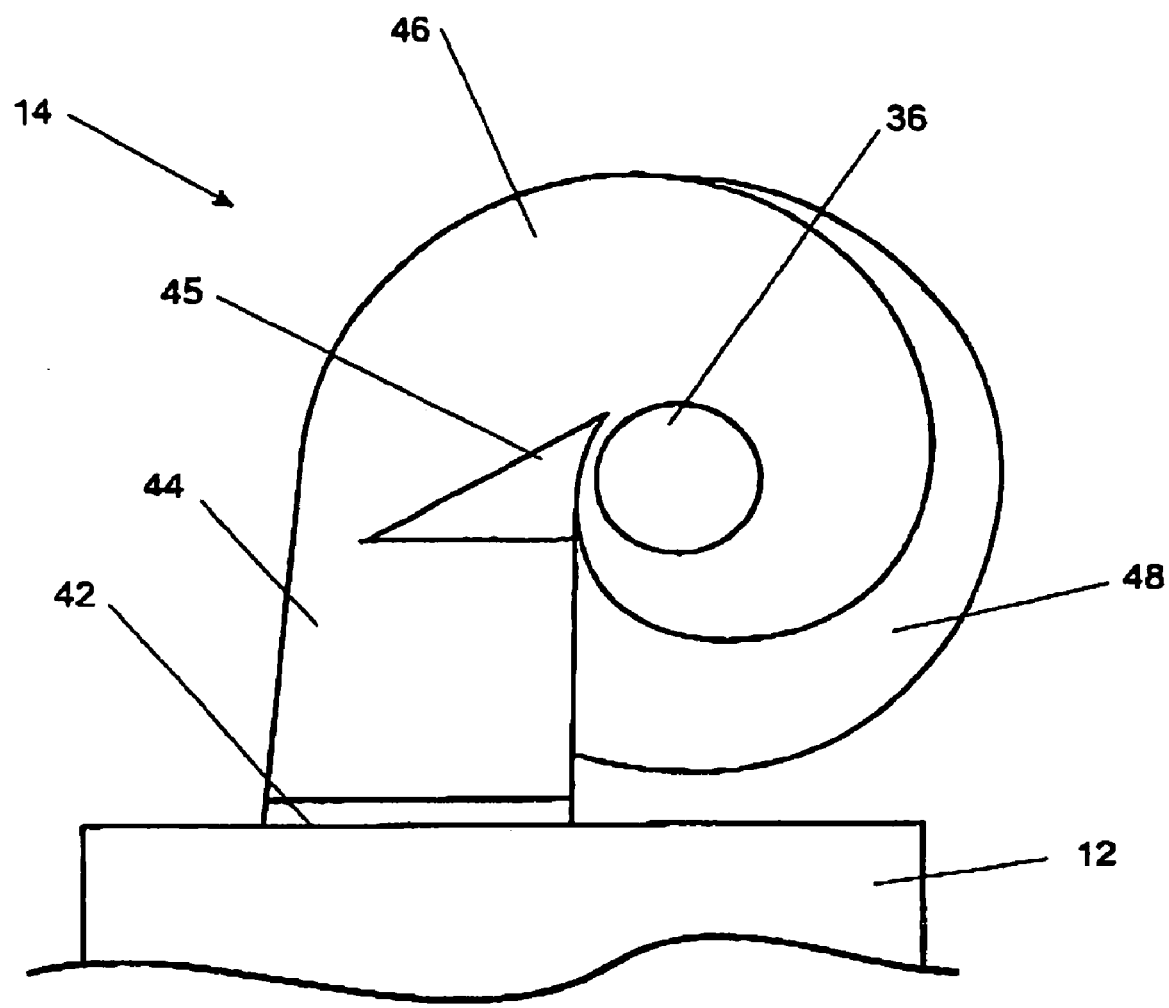
FIG. 3 is a top plan view of a funnel for supplying water from the infeed tank into the top end of the treatment tube of the apparatus according to one embodiment of the invention.

The funnel 14 leading from the edge of infeed tank 12 into the top of ultraviolet radiation chamber 10 is shown in plan view in FIG. 3. An opening though a side of infeed tank 12 through which an aqueous solution containing floating comestibles passes is provided above weir 42. From weir 42 a downward sloping sluiceway 44 leads over a steeply sloping portion 45 down a scrolling portion 46 and into the top of passage 36. A sloping side 48 completes the passageway from the top edge of funnel 14 down to the scrolling portion 46. The funnel 14 constitutes a means for providing a feed of the cut comestibles and water through the tube into its first end in a manner which establishes a vortex flow over at least the part of its vertically oriented length of the tube.

Figure 2:
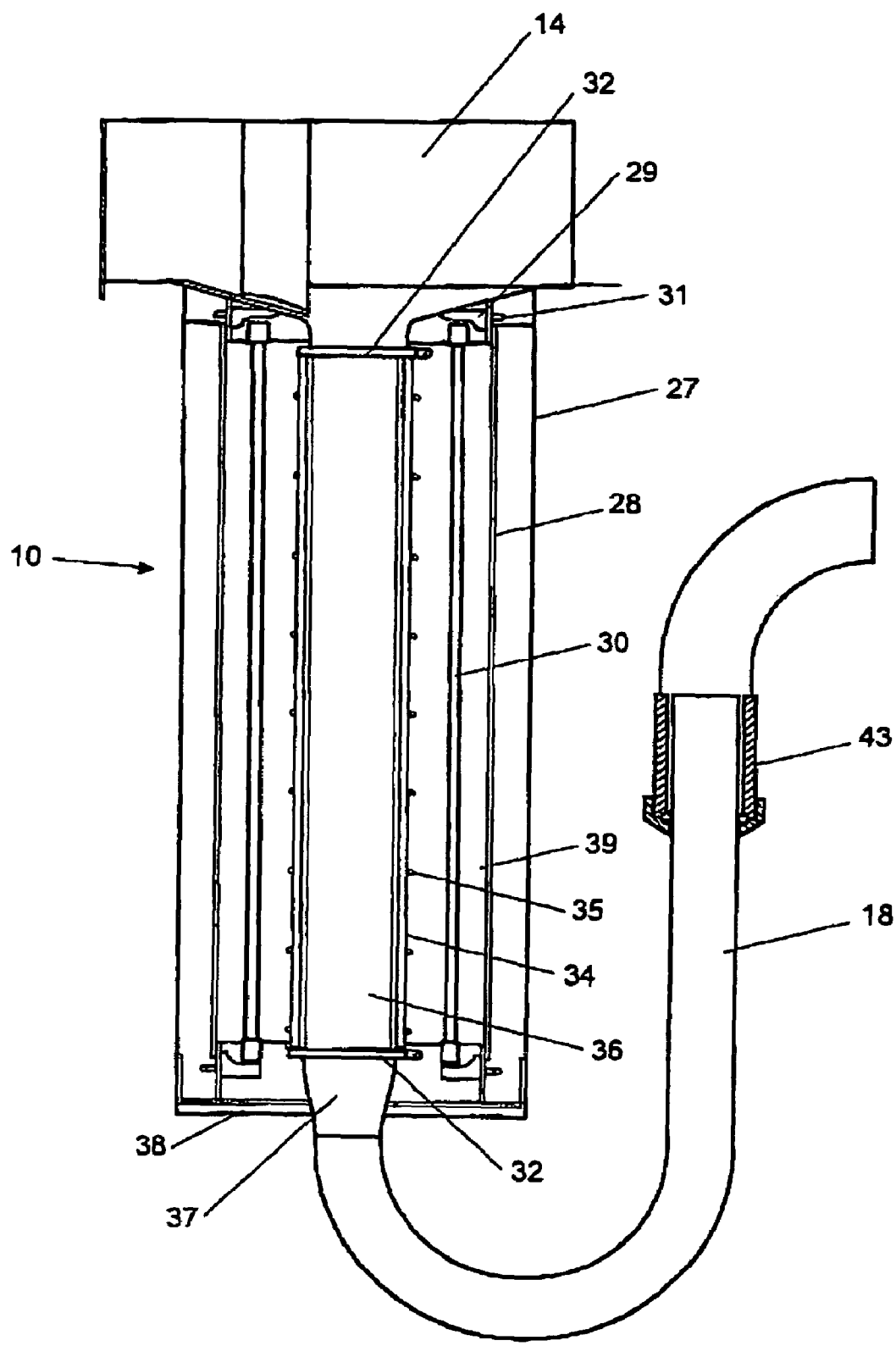
FIG. 2 is a side elevation sectional view of a preferred embodiment of the ultraviolet treatment portion of the apparatus according to the invention.
Figure 5:
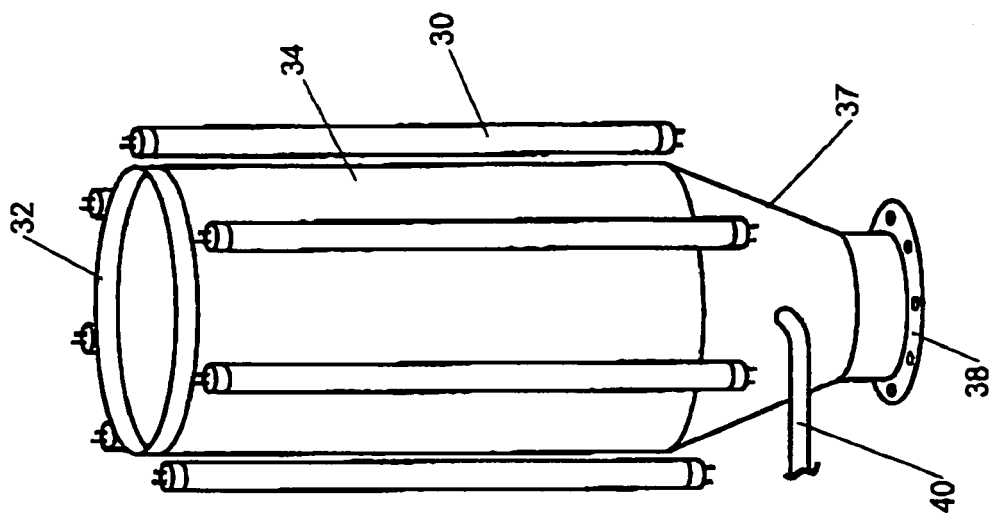
FIG. 5 is an isometric view, partly exploded, of the embodiment shown in FIG. 4.
Figure 4:
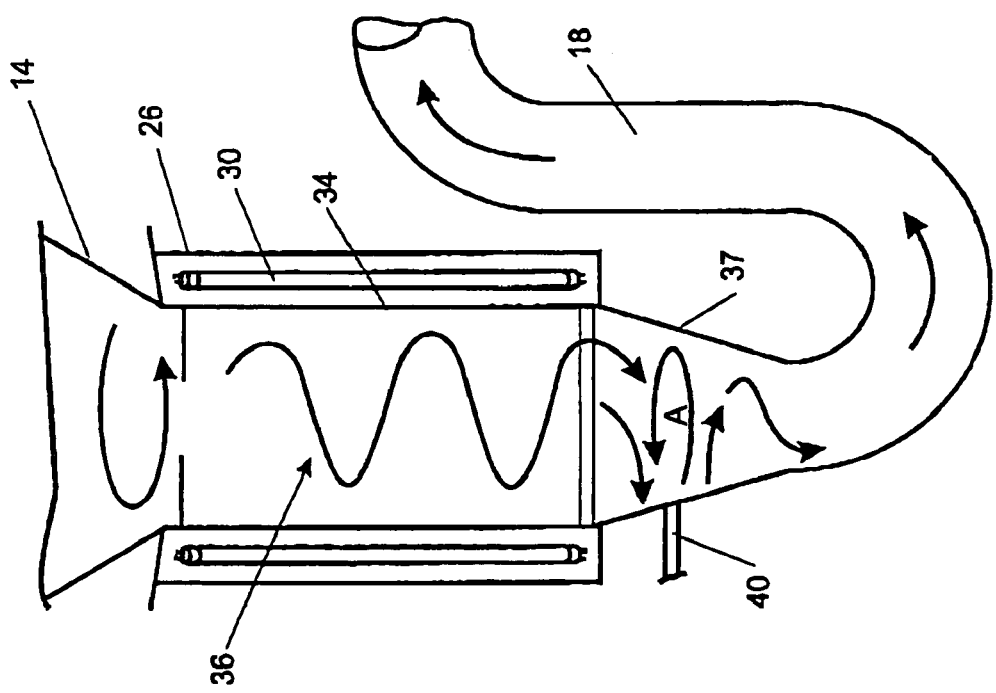
FIG. 4 is a side elevation sectional view of an alternative embodiment of the portion of the apparatus shown in FIG. 2.

In the embodiments illustrated in FIGS. 4 and 5 the passageway 36 is shorter and has a greater diameter than that illustrated in FIG. 2. Otherwise the componentry and the construction is substantially the same. In addition there is provided an auxiliary tangential jet 40 which injects water into funnel-shaped portion 37 as shown by the arrow A in FIG. 4. The injection of this jet has an effect on the flow through rate of the vortex formed within passageway 36 as will be explained below. Jet 40 is connected to a source of high pressure water.

Figure 6:
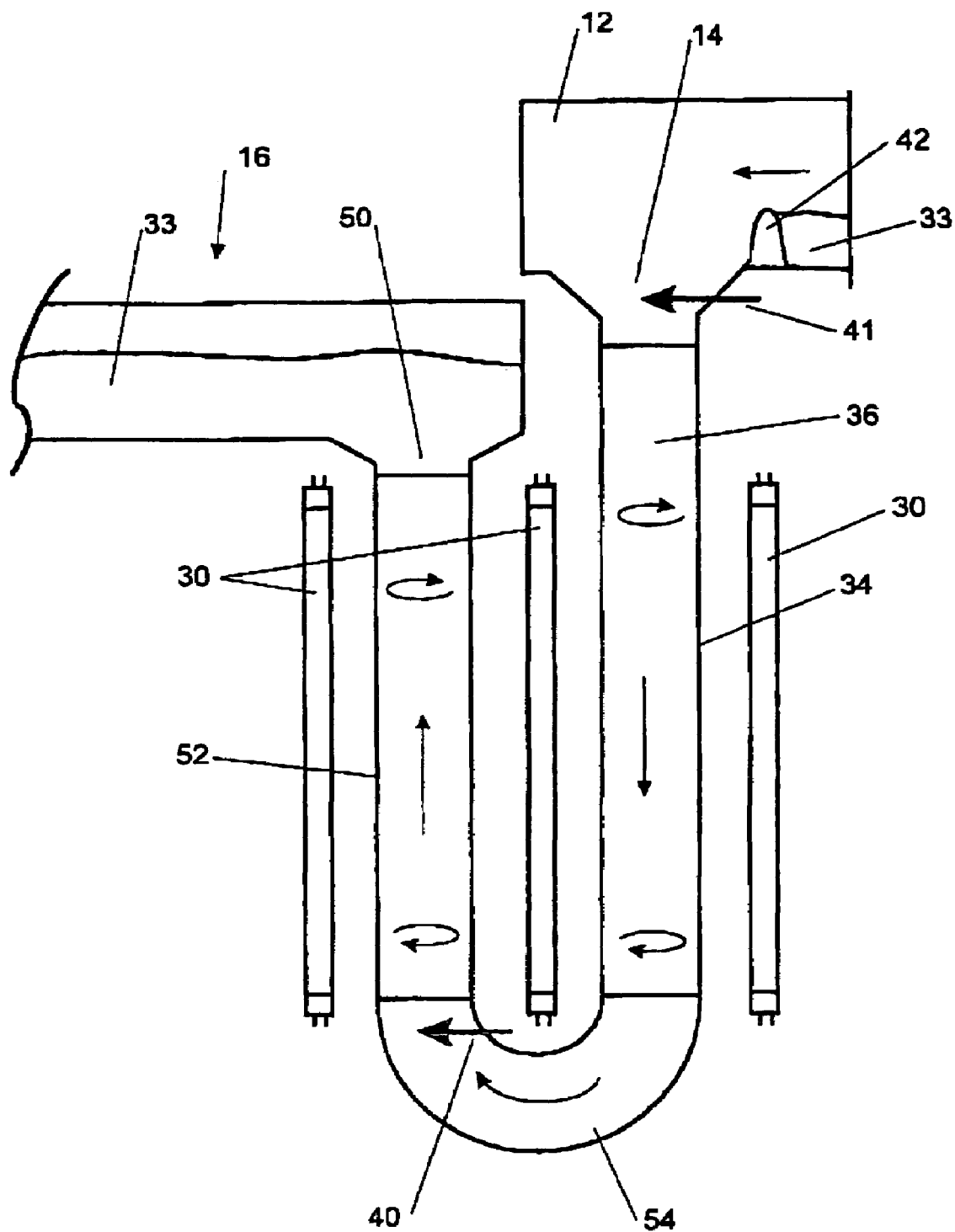
FIG. 6 is side elevational view of another alternative embodiment of the invention which is particularly effective in treating waste water.

In the embodiment illustrated in FIG. 6 infeed tank 12 is positioned to be at a slightly higher elevation than holding tank 16 so as to provide an appropriate head. A passage 36 from infeed tank 12 to holding tank 16 is defined, in the downstream direction, by a funnel 14 which joins a first AFP tube 34, an elbow portion 54 followed by a second AFP tube 52 and an outlet 50.

A weir 42 is provided in infeed tank 12 at the mouth of funnel 14. Funnel 14 is of the type illustrated in FIG. 3. However, it is provided with a water jet 41 which is directed tangentially into funnel 14 adjacent the upper end of the first AFP tube 34. The volume and velocity of water jet 41 can be controlled with, for example, a common water tap valve.

Three ultraviolet tubes 30 are illustrated. In this embodiment a casing (not shown) surrounds the total irradiating portion of the apparatus, that is both AFP tubes 34, and to the outside of the outer ring of UV tubes 30.

A second water jet 40 also directed tangentially into elbow 54 can optionally be provided. It too has a control valve in common with waterjet 41.

Operation of the Apparatus

The overall operation of the apparatus will be explained with reference to FIG. 1. Comestibles, for example sliced apples, are placed on infeed conveyor 11 and fed down a chute 26 into the treatment fluid 33 in infeed tank 12. Treatment fluid 33 contains preservatives. The preferred aqueous treatment solution will contain 1–7% W/W calcium hydroxide.

Inflow of recycled treatment fluid 33 over weir 25 causes a flow across infeed tank 12 and over weir 42 into the funnel 14. As the fluid 33 containing the pieces of fruit travels down the scrolling pathway 46 it establishes a vortex which then swirls down passageway 36 through the ultraviolet radiation chamber 10.

In the embodiment illustrated in FIGS. 1 and 3 the flow rate of the turbulated vortex is not able to be varied. In the embodiments shown in FIGS. 4 to 6 the speed of the turbulated vortex is able to be varied by the tangential injection of a jet of water within the main flow. The flow valves of the water jets 40 and 41 are able to control their flow rate. The faster the speed of the turbulated vortex, the longer is the residence time in the AFP tube or tubes.

The effectiveness of ultraviolet treatment depends on the length of exposure to the radiation, the wavelength of the radiation and the temperature at which the radiation is applied. The advantage of forming a vortex within passageway 36 is that it allows for a controlled dwell time in passage 36 during which it is exposed to the radiation. The pieces of fruit within the vortex may remain more or less stationary depending on the speed with which the vortex descends down the passage 36. A vortex, effective in suspending the pieces within the radiation chamber momentarily, can be achieved by the use of an infeed funnel 14 as described with reference to FIG. 3.

The optimum temperature of 42.2° C. to achieve best disinfection using the particular tube described above can be achieved within the chamber by the heat generated by the ultraviolet tubes. Temperatures up to 50° C. can be employed. A thermostat and air conditioning may maintain the temperature at the desired level.

Once the treatment has been completed in ultraviolet radiation chamber 10 the pieces of fruit are discharged out pipe 18 into the holding tank 16. The conveyor 13 travels in a clockwise direction. The upper lap of the conveyor 13 picks up pieces of fruit and discharges them onto a further conveyor 17. From conveyor 17 they are taken for further treatment, usually involving drying and packaging. Because of the disinfection by exposure to ultraviolet radiation the pieces of fruit will then have an enhanced shelf life once they are packaged in sterile packaging.

Treatment fluid 33 in holding tank 16 will overflow into the top of pipe 19 and be discharged into main tank 21. Make up treatment fluid 33 may be added to main tank 21 as required.

Pump 22 then pumps treatment fluid 33 through return pipe 20 in the direction of arrow B through a filtration system 23 and up pipe 24 over weir 25 where it completes the circuit by refilling infeed tank 12. A means to recycle water from the holding tank 16 to the in-feed tank 12 includes the main tank 21, the pipe 19 discharging water from the holding tank 19 to the main tank 21, pipes 20, 24 forming conduit means from the main tank 21 to the in-feed tank 12, a pump 22 and a filtering means 23 in the conduit means, the distal end of the conduit means returning water into the in-feed tank.

The method has been described in relation to pieces of cut fruit. However, it can be used for any form of comestible which can benefit from disinfection through ultraviolet radiation.

The embodiment illustrated in FIG. 6 may be used in conjunction with tanks 12, 16 and 21 illustrated in FIG. 1. It offers compactness in height between infeed tank 12 and holding tank 16 while providing a residence time for UV radiation equivalent to that achieved if tubes 34 and 52 were end to end. The positioning of outlet 50 at the bottom of tank 16 also reduces the overall height of the apparatus. When the flow of treatment fluid 33 is stopped in infeed tank 2 the level of fluid in tube 34 is that of fluid in holding tank 16.

The invention has been described with particular reference to the treatment of comestibles. During such treatment the UV radiation kills or inhibits the growth of microorganisms on comestibles. It is the microorganisms which cause the degradation of the comestibles.

The apparatus and method of the invention can also be used to kill or inhibit growth of microorganisms in waste water. A waste water treatment apparatus would not require means for recovery of comestibles and would be a continuous flow system rather than the closed loop system shown in FIG. 1.

Where the waste water is particularly cloudy a source of UV radiation of higher intensity may be used in addition to means to increase the dwell time in the treatment chamber. Additional tubes and loops additional to those illustrated in FIG. 6 may be employed. Tangential water jets with higher velocity may be employed to increase the vortex turbulated flow rate. This increases the radial moments of force and decreases the axial moments of force along flow path 36. This in turn means the waste water advances more slowly along flow path 36 and hence its dwell time in the chamber is increased.

Although the invention has been described through the use of a low pressure mercury vapour quartz ultraviolet radiating tube at its optimum temperature, other sources and conditions of ultraviolet radiation known to those skilled in the art may be used.

Other permutations and combinations of the invention will be apparent to those skilled in the art.

The invention claimed is:

1. An apparatus for treating cut comestible(s) with ultraviolet light to at least reduce the presence of microorganisms on the cut comestible(s), the apparatus comprising:
   a tube which is transparent to ultraviolet radiation and having at least a part of its length vertically oriented, said tube having a first end and a second end, said first end being higher than the second end;
   means for providing a feed of the cut comestible(s) and water through the tube into said first end in an manner which establishes a vortex flow over at least the part of its vertically oriented length of said tube,
   ultraviolet radiating means surrounding said tube to radiate ultraviolet radiation into said tube over at least the part of its vertically oriented length;
   a holding tank for receiving water and the cut comestibles from the second end of the tube; and
   an outlet feed conveyor for removing the cut comestible(s) from the holding tank.

2. The apparatus as claimed in claim 1 wherein said tube is constructed of a fluoropolymer.

3. The apparatus as claimed in claim 1 wherein said ultraviolet radiating means is a low pressure mercury vapour quartz tube.

4. The apparatus as claimed in claim 3 wherein said low pressure mercury vapour quartz tube radiates ultraviolet radiation at a wavelength of 253.7 nanometers.

5. The apparatus as claimed in claim 1 wherein there is a casing surrounding said ultraviolet radiating means, the inner face of said casing having reflecting means for reflecting ultraviolet radiation.

6. The apparatus as claimed in claim 1 wherein the water contains calcium hydroxide.

7. The apparatus as claimed in claim 1 wherein there is provided an infeed tank upstream of said means for providing a feed of the cut comestible(s) and water through the tube into said first end in an manner which establishes a vortex flow over at least the part of its vertically oriented length of said tube.

8. The apparatus as claimed in claim 1 wherein there is a means for continuously feeding comestibles into said infeed tank.

9. The apparatus as claimed in claim 1 wherein said cut comestibles are subject to treatment fluid in the holding tank.

10. The apparatus as claimed in claim 1 wherein a recirculation system returns water from the holding tank to the means for providing a feed of the cut comestible(s) and water through the tube into said first end in an manner which establishes a vortex flow over at least the part of its vertically oriented length of said tube.

11. An apparatus for killing or inhibiting the growth of microorganisms in water which comprises: a vertically oriented tube which is transparent to ultraviolet radiation, said tube having a top end and a bottom end, means to supply water into said top end in an manner which establishes a vortex flow in said tube, ultraviolet radiating means surrounding said tube adapted to radiate ultraviolet radiation through said tube and water containing said microorganisms therein, and draining means from said bottom end of said tube, wherein said means for supplying said water into said tube comprises a funnel having a spiral flow path therethrough.

12. The apparatus as claimed in claim 11 wherein there is provided a tangential water jet to impart a controllable vortex turbulation within said tube in combination with said funnel.

13. An apparatus for killing or inhibiting the growth of microorganisms in water which comprises: a vertically oriented tube which is transparent to ultraviolet radiation, said tube having a top end and a bottom end, an in-feed tank, means to supply water from said in-feed tank into said top end in an manner which establishes a vortex flow in said tube, ultraviolet radiating means surrounding said tube adapted to radiate ultraviolet radiation through said tube and water containing said microorganisms therein, and draining means from said bottom end of said tube,
   wherein there is a holding tank downstream of said draining means into which said draining means may discharge water and comestibles that have passed through said tube; and
   wherein there are means for recycling water from said holding tank to said infeed tank.

14. The apparatus as claimed in claim 13 wherein said means to recycle said water comprises a main tank, a pipe discharging water from said holding tank to said main tank, conduit means from said main tank to said infeed tank, a pump and a filtering system in said conduit means, the distal end of said conduit means returning water into said infeed tank.

* * * * *